US012741021B2

(12) United States Patent
Onita

(10) Patent No.: US 12,741,021 B2
(45) Date of Patent: Sep. 22, 2026

(54) PREPARATION INCLUDING VACCINE ADJUVANT

(71) Applicant: Sumitomo Pharma Co., Ltd., Osaka (JP)

(72) Inventor: Maiko Onita, Osaka (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 1429 days.

(21) Appl. No.: 17/417,871

(22) PCT Filed: Dec. 25, 2019

(86) PCT No.: PCT/JP2019/050947

§ 371 (c)(1),
(2) Date: Jun. 24, 2021

(87) PCT Pub. No.: WO2020/138217

PCT Pub. Date: Jul. 2, 2020

(65) Prior Publication Data

US 2022/0072126 A1 Mar. 10, 2022

(30) Foreign Application Priority Data

Dec. 26, 2018 (JP) ................................ 2018-242614

(51) Int. Cl.

| | |
|---|---|
| ***A61K 39/395*** | (2006.01) |
| ***A61K 9/19*** | (2006.01) |
| ***A61K 39/39*** | (2006.01) |
| ***A61K 47/06*** | (2006.01) |
| ***A61K 47/14*** | (2017.01) |
| ***A61K 47/22*** | (2006.01) |
| ***A61K 47/26*** | (2006.01) |
| *A61K 39/00* | (2006.01) |

(52) U.S. Cl.

CPC ................ *A61K 39/39* (2013.01); *A61K 9/19* (2013.01); *A61K 47/06* (2013.01); *A61K 47/14* (2013.01); *A61K 47/22* (2013.01); *A61K 47/26* (2013.01); *A61K 2039/55511* (2013.01)

(58) Field of Classification Search

None

See application file for complete search history.

(56) References Cited

U.S. PATENT DOCUMENTS

| | | | | |
|---|---|---|---|---|
| 10,632,192 | B2 * | 4/2020 | Kimura .................. | A61K 39/39 |
| 11,833,247 | B2 * | 12/2023 | Fukushima ............ | A61K 47/69 |
| 11,911,466 | B2 * | 2/2024 | Kimura ................... | A61P 37/04 |
| 12,059,462 | B2 * | 8/2024 | Takahashi ............. | A61K 39/39 |
| 2003/0215497 | A1 | 11/2003 | Leesman | |
| 2014/0065179 | A1 | 3/2014 | Nozaki et al. | |
| 2018/0280499 | A1 | 10/2018 | Kimura et al. | |
| 2020/0121600 | A1 | 4/2020 | Fukushima | |

FOREIGN PATENT DOCUMENTS

| | | |
|---|---|---|
| EP | 3827842 | 6/2021 |
| JP | 2001-151699 | 6/2001 |
| WO | WO 2012/124631 | 9/2012 |
| WO | WO 2017/061532 | 4/2017 |
| WO | WO 2018/181420 | 10/2018 |
| WO | WO 2020/022272 | 1/2020 |

OTHER PUBLICATIONS

Allison, Methods, vol. 19, pp. 87-93 (Year: 1999).*

International Preliminary Report on Patentability in International Appln. No. PCT/JP2019/050947, mailed Jul. 8, 2021, 17 pages (with English translation).

International Search Report and Written Opinion in International Appln. No. PCT/JP2019/050947, dated Mar. 17, 2020, 21 pages (with English translation).

Traquina et al., “MF59 Adjuvant Enhances the Antibody Response to Recombinant Hepatitis B Surface Antigen Vaccine in Primates,” Journal of Infectious Diseases, Dec. 1996, 174(6): 1168-1175.

Yarkoni et al., “Eradication by Active Specific Immunotherapy of Established Tumor Transplants and Microscopic Lymph Node Metastases,” Cancer Research, Jul. 1982, 42(7):2544-2546.

Extended European Search Report in European Appln. No. 19905802.5, dated Nov. 10, 2022, 7 pages.

Suzuki, “A New Method for Highly Stabilizing Emulsions,” Technical Information Institute Co., Ltd., 2004, Partial English Translation, 9 pages.

* cited by examiner

*Primary Examiner* — Yunsoo Kim

(74) *Attorney, Agent, or Firm* — Fish & Richardson P.C.

(57) ABSTRACT

Provided is a composition that is useful as a vaccine adjuvant and has excellent storage stability and immunostimulatory activity. Specifically provided is a freeze-dried preparation that has high storage stability, said preparation containing a (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide, squalane, a hydrophilic surfactant, and an oleophilic surfactant, and being characterized by containing an ascorbic acid-based antioxidant and an excipient.

28 Claims, No Drawings

PREPARATION INCLUDING VACCINE ADJUVANT

TECHNICAL FIELD

The present invention relates to an emulsion composition of a compound useful for a vaccine adjuvant and a lyophilized formulation of the composition.

BACKGROUND ART

A subunit vaccine that uses a part of components of a pathogen as an antigen can be produced by technique such as chemical synthesis and genetic recombination technology, and is more advantageous than a vaccine that uses a pathogen itself in terms of its safety and producing processes. Whereas, a subunit vaccine tends to have a lower immunostimulatory activity than a live vaccine or inactivated vaccine that uses a pathogen itself. In view of this, a preventive or therapeutic method has been studied to use an adjuvant in combination with a vaccine antigen in order to reinforce the immunogenicity of an epitope and enhance the immunostimulatory activity of a vaccine.

Adjuvants having a TLR7 agonist activity have been reported recently, including (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide (hereinafter, referred to as "Compound A") (Patent Literature 1).

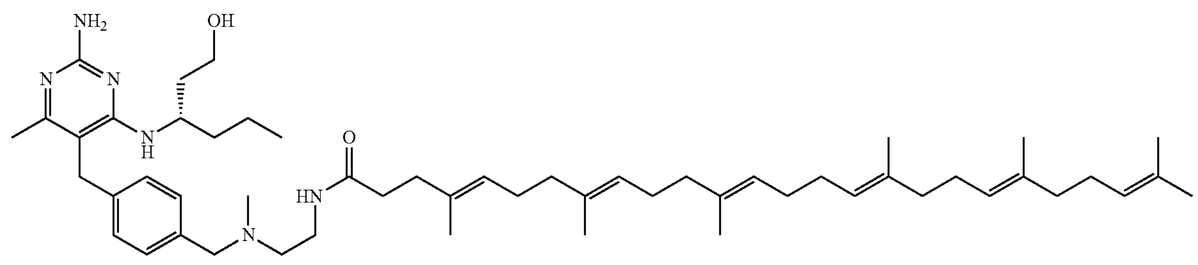 [SMILES: CCC[C@@H](CCO)Nc1nc(N)nc(C)c1Cc1ccc(CN(C)CCNC(=O)CC/C(C)=C/CC/C(C)=C/CC/C(C)=C/CC/C=C(\C)CC/C=C(\C)CCC=C(C)C)cc1]

Compound A has a good vaccine-adjuvant activity, but it is desired to formulate it into a pharmaceutical formulation such as an emulsion for the purpose of administration to a mammal as a vaccine adjuvant. Generally, it is known that an antioxidant derived from ascorbates is used to improve the preservation stability of an emulsion formulation. It has not been known, however, that an antioxidant derived from ascorbate derivatives can stabilize the particle size distribution.

CITATION LIST

Patent Literature

Patent Literature 1 WO 2017/061532

SUMMARY OF INVENTION

Problems to be Solved by the Invention

The present invention provides a formulated composition useful as a vaccine adjuvant with good preservation stability and immunostimulatory activity.

Means of Solving the Problems

Compound A has six unsaturated bonds derived from a squalene-type structure in its molecule. In studies of formulation of Compound A, it has become evident that when Compound A is formulated into common lyophilized a formulation of an emulsion formulation that uses squalene as an oil ingredient, the intramolecular unsaturated bonds of Compound A are oxidized, resulting in the reduction of contents of Compound A. The inventor has extensively studied to find out a feasible pharmaceutical formulation comprising a vaccine adjuvant with a high preservation stability, and then has found that the stability to oxidation of Compound A is improved by the use of squalane as an oil ingredient in the preparation of an emulsion composition comprising Compound A. It has also been found that addition of an antioxidant of ascorbate derivatives allows for the provision of a pharmaceutical formulation with a good preservation stability, in particular not only the stability to oxidation of Compound A itself but also the stability of particle size distribution, and the present invention has been achieved.

Specifically, a summary of the present invention is as follows.

Item 1

A lyophilized formulation of an emulsion comprising:

i) (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide (hereinafter referred to as "Compound A"), or a pharmaceutically acceptable salt thereof;

ii) squalane;

iii) an antioxidant A selected from the group consisting of an ascorbate ester (e.g., L-ascorbic stearate, ascorbyl palmitate, etc.), an inorganic salt of ascorbic acid (e.g., potassium ascorbate, sodium ascorbate, calcium ascorbate, etc.), and ascorbic acid; and iv) an excipient A selected from the group consisting of a non-reducing sugar and a sugar alcohol, provided that mannitol is excluded.

Item 2

The formulation according to Item 1, further comprising v) a hydrophilic surfactant and vi) a lipophilic surfactant.

Item 3

The formulation according to Item 1 or 2, wherein the emulsion is an oil-in-water emulsion.

Item 4

The formulation according to Item 2 or 3, wherein the hydrophilic surfactant is polyoxyethylene sorbitan fatty acid esters (e.g., Polysorbate 20, Polysorbate 40, Polysorbate 60, Polysorbate 65, Polysorbate 80, etc.); polyoxyethylene hydrogenated castor oils (e.g., polyoxyethylene hydrogenated castor oil 10, polyoxyethylene hydrogenated castor oil 20, polyoxyethylene hydrogenated castor oil 40, polyoxyethylene hydrogenated castor oil 50, polyoxyethylene hydrogenated castor oil 60, etc.); or polyoxyethylene polyoxypropylene glycols (e.g., polyoxyethylene (42) polyoxypropylene (67) glycol, polyoxyethylene (54) polyoxypropylene (39) glycol, polyoxyethylene (105) polyoxypropylene (5) glycol, polyoxyethylene (124) polyoxypropylene (39) glycol, polyoxyethylene (160) polyoxypropylene (30) glycol, polyoxyethylene (196) polyoxypropylene (67) glycol, polyoxyethylene (200) polyoxypropylene (70) glycol, etc.).

Item 5

The formulation according to Item 2 or 3, wherein the hydrophilic surfactant is Polysorbate 20, Polysorbate 40, Polysorbate 80, polyoxyethylene hydrogenated castor oil 60, or polyoxyethylene (160) polyoxypropylene (30) glycol.

Item 6.

The formulation according to Item 2 or 3, wherein the hydrophilic surfactant is Polysorbate 20, Polysorbate 40, or Polysorbate 80.

Item 7

The formulation according to any one of Items 2 to 6, wherein the lipophilic surfactant is sorbitan fatty acid esters (e.g., sorbitan fatty acid ester, sorbitan monolaurate, sorbitan monopalmitate, sorbitan monostearate, sorbitan tristearate, sorbitan monooleate, sorbitan sesquioleate, sorbitan trioleate, medium-chain triglyceride, etc.); glycerin fatty acid esters (e.g., glycerin fatty acid ester, glyceryl monostearate, glyceryl monomyristate, glyceryl monooleate, glyceryl triisooctanoate, etc.); sucrose fatty acid esters (e.g., sucrose fatty acid ester, sucrose stearate, sucrose palmitate, etc.); or propylene glycol fatty acid esters (e.g., propylene glycol fatty acid ester, propylene glycol monostearate, etc.).

Item 8

The formulation according to any one of Items 2 to 6, wherein the lipophilic surfactant is sorbitan fatty acid ester, sorbitan monooleate, sorbitan sesquioleate, or sorbitan trioleate.

Item 9

The formulation according to any one of Items 2 to 6, wherein the lipophilic surfactant is sorbitan trioleate.

Item 10

The formulation according to any one of Items 1 to 9, further comprising an antioxidant B selected from the group consisting of tocopherol (e.g., α-tocopherol, β-tocopherol, γ-tocopherol, δ-tocopherol, etc.); tocopherol acetate; and butyl hydroxyanisole.

Item 11

The formulation according to Item 10, wherein the antioxidant B is tocopherol selected from the group consisting of α-tocopherol, β-tocopherol, γ-tocopherol, and δ-tocopherol.

Item 12

The formulation according to Item 10, wherein the antioxidant B is α-tocopherol.

Item 13

The formulation according to any one of Items 1 to 12, wherein the antioxidant A is ascorbyl palmitate, potassium ascorbate, sodium ascorbate, or ascorbic acid.

Item 14

The formulation according to any one of Items 1 to 12, wherein the antioxidant A is sodium ascorbate or potassium ascorbate.

Item 15

The formulation according to any one of Items 1 to 14, wherein the excipient A is a non-reducing sugar (e.g., sucrose, and trehalose); or a sugar alcohol (e.g., sorbitol, erythritol, xylitol, maltitol, and lactitol).

Item 16

The formulation according to any one of Items 1 to 14, wherein the excipient A is sucrose, trehalose, sorbitol, or xylitol.

Item 17

The formulation according to any one of Items 1 to 14, wherein the excipient A is sucrose or trehalose.

Item 18

The formulation according to any one of Items 1 to 17, wherein the blending amount of squalane is 50 to 500 times the weight of Compound A.

Item 19

The formulation according to any one of Items 1 to 17, wherein the blending amount of squalane is 100 to 400 times the weight of Compound A.

Item 20

The formulation according to any one of Items 1 to 17, wherein the blending amount of squalane is 200 to 300 times the weight of Compound A.

Item 21

The formulation according to any one of Items 2 to 20, wherein the blending amount of the hydrophilic surfactant is 0.5 to 250 times the weight of Compound A.

Item 22

The formulation according to any one of Items 2 to 20, wherein the blending amount of the hydrophilic surfactant is 5 to 100 times the weight of Compound A.

Item 23

The formulation according to any one of Items 2 to 20, wherein the blending amount of the hydrophilic surfactant is 10 to 50 times the weight of Compound A.

Item 24

The formulation according to any one of Items 2 to 21, wherein the blending amount of the lipophilic surfactant is 0.5 to 250 times the weight of Compound A.

Item 25

The formulation according to any one of Items 2 to 22, wherein the blending amount of the lipophilic surfactant is 5 to 100 times the weight of Compound A.

Item 26

The formulation according to any one of Items 2 to 23, wherein the blending amount of the lipophilic surfactant is 10 to 50 times the weight of Compound A.

Item 27

The formulation according to any one of Items 1 to 26, wherein the blending amount of the antioxidant A is 0.5 to 500 times the weight of Compound A in terms of the weight of sodium ascorbate.

Item 28

The formulation according to any one of Items 1 to 26, wherein the blending amount of the antioxidant A is 2.5 to 250 times the weight of Compound A in terms of the weight of sodium ascorbate.

Item 29

The formulation according to any one of Items 1 to 26, wherein the blending amount of the antioxidant A is 5 to 100 times the weight of Compound A in terms of the weight of sodium ascorbate.

Item 30

The formulation according to any one of Items 1 to 29, wherein the blending amount of the excipient A is 50 to 1000 times the weight of Compound A.

Item 31

The formulation according to any one of Items 1 to 29, wherein the blending amount of the excipient A is 100 to 750 times the weight of Compound A.

Item 32

The formulation according to any one of Items 1 to 29, wherein the blending amount of the excipient A is 200 to 625 times the weight of Compound A.

Item 33

The formulation according to any one of Items 10 to 32, wherein the blending amount of the antioxidant B is 5 to 250 times the weight of Compound A.

Item 34

The formulation according to any one of Items 10 to 32, wherein the blending amount of the antioxidant B is 12.5 to 125 times the weight of Compound A.

Item 35

The formulation according to any one of Items 10 to 32, wherein the blending amount of the antioxidant B is 25 to 50 times the weight of Compound A.

Item 36

The formulation according to any one of Items 1 to 35, wherein the weight of Compound A is 0.0001 to 0.65 times the weight obtained by excluding Compound A from the lyophilized formulation.

Item 37

The formulation according to any one of Items 1 to 35, wherein the weight of Compound A is 0.0002 to 0.35 times the weight obtained by excluding Compound A from the lyophilized formulation.

Item 38

The formulation according to any one of Items 1 to 35, wherein the weight of Compound A is 0.0005 to 0.065 times the weight obtained by excluding Compound A from the lyophilized formulation.

Item 39

The formulation according to any one of Items 1 to 38, wherein both $D_{90}$ values of particle sizes of an emulsion immediately after preparation and an emulsion reconstituted after 6-month storage at 25° C. as the lyophilized formulation are 1000 nm or less.

Item 40

The formulation according to any one of Items 1 to 39, wherein an increased amount in the area percentage values of an impurity UK-1.02 after 6-month storage at 5° C. as the lyophilized formulation is 5.0% or less.

Item 41

The formulation according to any one of Items 1 to 39, wherein an increased amount in the area percentage values of an impurity UK-1.02 after 6-month storage at 5° C. as the lyophilized formulation is 1.0% or less.

Item 42

A vaccine adjuvant comprising the formulation according to any one of Items 1 to 41.

Item 43

A vaccine comprising the formulation according to any one of Items 1 to 41 and an antigen.

Item 44

The vaccine according to Item 43, wherein the antigen is derived from a pathogen.

Item 45

A kit comprising the formulation according to any one of Items 1 to 41 and an antigen.

Item 46

A lyophilized formulation of an emulsion comprising:

i) (4E,8E,12E,16E,20E)-N-{2-[{4-[(2-amino-4-{[(3S)-1-hydroxyhexan-3-yl]amino}-6-methylpyrimidin-5-yl) methyl]benzyl}(methyl)amino]ethyl}-4,8,12,17,21,25-hexamethylhexacosa-4,8,12,16,20,24-hexaenamide, or a pharmaceutically acceptable salt thereof;

ii) squalane;

iii') tocopherol (e.g., α-tocopherol, β-tocopherol, γ-tocopherol, δ-tocopherol, etc.); and iv) an excipient A selected from the group consisting of a non-reducing sugar and a sugar alcohol, provided that mannitol is excluded.

Item 47

The formulation according to Item 46, further comprising:

v) a hydrophilic surfactant selected from Polysorbate 20, Polysorbate 40, or Polysorbate 80; and vi) a lipophilic surfactant selected from sorbitan fatty acid ester, sorbitan monooleate, sorbitan sesquioleate, or sorbitan trioleate.

Item 48

An emulsion comprising:

i) (4E,8E,12E,16E,20E)-N-{2-[{4-[(2-amino-4-{[(3S)-1-hydroxyhexan-3-yl]amino}-6-methylpyrimidin-5-yl) methyl]benzyl}(methyl)amino]ethyl}-4,8,12,17,21,25-hexamethylhexacosa-4,8,12,16,20,24-hexaenamide, or a pharmaceutically acceptable salt thereof;

ii) squalane;

iii) an antioxidant A selected from the group consisting of an ascorbate ester (e.g., L-ascorbic stearate, ascorbyl palmitate, etc.), an inorganic salt of ascorbic acid (e.g., potassium ascorbate, sodium ascorbate, calcium ascorbate, etc.), and ascorbic acid; and iv) an excipient A selected from the group consisting of a non-reducing sugar and a sugar alcohol, provided that mannitol is excluded.

Item 49

The emulsion according to Item 48, further comprising v) a hydrophilic surfactant and vi) a lipophilic surfactant.

Item 50

The emulsion according to Item 48 or 49, further comprising an antioxidant B selected from the group consisting of tocopherol (e.g., α-tocopherol, β-tocopherol, γ-tocopherol, δ-tocopherol, etc.); tocopherol acetate; and butyl hydroxyanisole.

Item 51

An emulsion comprising:

i) (4E,8E,12E,16E,20E)-N-{2-[{4-[(2-amino-4-{[(3S)-1-hydroxyhexan-3-yl]amino}-6-methylpyrimidin-5-yl) methyl]benzyl}(methyl)amino]ethyl}-4,8,12,17,21,25-hexamethylhexacosa-4,8,12,16,20,24-hexaenamide, or a pharmaceutically acceptable salt thereof;

ii) squalane;

iii') tocopherol (e.g., α-tocopherol, β-tocopherol, γ-tocopherol, δ-tocopherol, etc.); and iv) an excipient A selected from the group consisting of a non-reducing sugar and a sugar alcohol, provided that mannitol is excluded.

Effect of the Invention

The present invention can enhance an antigen-specific immune reaction, resulting in the provision of a vaccine adjuvant formulation with high preservation stability.

DESCRIPTION OF EMBODIMENTS

The formulation of the present invention is a lyophilized formulation of an emulsion comprising Compound A, squalane, an antioxidant A of ascorbates, and an excipient A. The present invention includes an emulsion formulation before lyophilization and an emulsion formulation after reconstitution of a lyophilized formulation.

Compound A comprised as an active ingredient in the formulation of the present invention may be a free form or a pharmaceutically acceptable acid addition salt or base addition salt thereof. Exemplary acid addition salts include acid addition salts with inorganic or organic acids such as hydrochloric acid, hydrobromic acid, sulfuric acid, trifluoroacetic acid, citric acid, and maleic acid. Exemplary base addition salts include alkali metal salts such as a sodium salt and a potassium salt, alkaline-earth metal salts such as a calcium salt, and an ammonium salt. Compound A or a pharmaceutically acceptable salt thereof in the present invention may also exist in the form of a hydrate or a solvate, and these forms are also encompassed in Compound A or a pharmaceutically acceptable salt thereof in the present invention. Details and production processes of these forms are described in Patent Literature 1, and Compound A or a pharmaceutically acceptable salt thereof may be prepared according to, for example, methods described in Patent Literature 1.

In the formulation of the present invention, the content of Compound A is described in terms of the content of a free form of Compound A. When Compound A is used as a pharmaceutically acceptable salt thereof, the content of Compound A is converted to the weight obtained by adding the weight of the salt to the weight of Compound A.

The term "emulsion" in the present invention means an oil-in-water emulsion or a water-in-oil emulsion, and is preferably an oil-in-water emulsion. The ratio (by weight) of an oil composition to an aqueous solution ranges preferably from 1:99 to 15:85, more preferably from 2:98 to 10:90, further preferably from 3:97 to 9:91, further more preferably from 4:96 to 7:93. Compound A exists in a state of being dissolved in an oil composition in an emulsion formulation of the present invention.

The term "lyophilized formulation" in the present invention means a formulation obtained by removing water from an emulsion formulation of the present invention under a lyophilization condition. Reconstitution of a lyophilized formulation with sterile water for injection in the weight of 2 to 20 times the weight of the lyophilized formulation can give an emulsion formulation.

An exemplary hydrophilic surfactant used herein includes polyoxyethylene sorbitan fatty acid esters (e.g., Polysorbate 20, Polysorbate 40, Polysorbate 60, Polysorbate 65, Polysorbate 80, etc.); polyoxyethylene hydrogenated castor oils (e.g., polyoxyethylene hydrogenated castor oil 10, polyoxyethylene hydrogenated castor oil 20, polyoxyethylene hydrogenated castor oil 40, polyoxyethylene hydrogenated castor oil 50, polyoxyethylene hydrogenated castor oil 60, etc.); and polyoxyethylene polyoxypropylene glycols (e.g., polyoxyethylene (42) polyoxypropylene (67) glycol, polyoxyethylene (54) polyoxypropylene (39) glycol, polyoxyethylene (105) polyoxypropylene (5) glycol, polyoxyethylene (124) polyoxypropylene (39) glycol, polyoxyethylene (160) polyoxypropylene (30) glycol, polyoxyethylene (196) polyoxypropylene (67) glycol, polyoxyethylene (200) polyoxypropylene (70) glycol, etc.), and a preferable hydrophilic surfactant is Polysorbate 20, Polysorbate 40, Polysorbate 80, polyoxyethylene hydrogenated castor oil 60, or polyoxyethylene (160) polyoxypropylene (30) glycol, further preferably Polysorbate 20, Polysorbate 40, or Polysorbate 80, particularly preferably Polysorbate 80.

The content of a hydrophilic surfactant in the formulation of the present invention ranges from 0.5 to 250 times, preferably from 5 to 100 times, further preferably from 10 to 50 times, the weight of Compound A.

An exemplary lipophilic surfactant used herein includes sorbitan fatty acid esters (e.g., sorbitan fatty acid ester, sorbitan monolaurate, sorbitan monopalmitate, sorbitan monostearate, sorbitan tristearate, sorbitan monooleate, sorbitan sesquioleate, sorbitan trioleate, medium-chain triglyceride, etc.); glycerin fatty acid esters (e.g., glycerin fatty acid ester, glyceryl monostearate, glyceryl monomyristate, glyceryl monooleate, glyceryl triisooctanoate, etc.); sucrose fatty acid esters (e.g., sucrose fatty acid ester, sucrose stearate, sucrose palmitate, etc.); and propylene glycol fatty acid esters (e.g., propylene glycol fatty acid ester, propylene glycol monostearate, etc.), and a preferable lipophilic surfactant is sorbitan fatty acid ester, sorbitan monooleate, sorbitan sesquioleate, or sorbitan trioleate, further preferably sorbitan trioleate.

The blending amount of a lipophilic surfactant in the formulation of the present invention ranges from 0.5 to 250 times, preferably from 5 to 100 times, further preferably from 10 to 50 times, the weight of Compound A.

As an oil ingredient in the formulation of the present invention, squalane is used. In the study of pharmaceutical formulations, the stability to oxidation of Compound A is improved when squalane is used instead of squalene which is commonly used as an oil ingredient in an emulsion formulation. Squalane is, therefore, preferable for an oil ingredient in the pharmaceutical formulation herein. The blending amount of squalane ranges from 50 to 500 times, preferably from 100 to 400 times, further preferably from 200 to 300 times, the weight of Compound A.

An exemplary antioxidant A used herein includes ascorbate esters (e.g., L-ascorbic stearate, ascorbyl palmitate, etc.); inorganic salts of ascorbic acid (e.g., potassium ascorbate, sodium ascorbate, calcium ascorbate, etc.); and ascorbic acid, and a preferable antioxidant A is ascorbyl palmitate, potassium ascorbate, sodium ascorbate, or ascorbic acid, further preferably sodium ascorbate or potassium ascorbate.

The content of an antioxidant A in the formulation of the present invention is defined in terms of the weight of sodium ascorbate. Specifically, the content obtained by conversion of the weight of ascorbic acid of an ascorbate derivative, an antioxidant A, into the weight of sodium ascorbate ranges from 0.5 to 500 times, preferably from 2.5 to 250 times, further preferably from 5 to 100 times, the weight of Compound A.

An exemplary excipient A used herein includes non-reducing sugars and sugar alcohols, provided that mannitol is excluded. It is preferably non-reducing sugars (e.g., sucrose, trehalose; and sugar alcohols (e.g., sorbitol, erythritol, xylitol, maltitol, and lactitol), further preferably sucrose, trehalose, sorbitol, or xylitol, further more preferably sucrose or trehalose, particularly preferably sucrose.

The content of an excipient A in the formulation of the present invention ranges from 50 to 1000 times, preferably from 100 to 750 times, further preferably from 200 to 625 times, the weight of Compound A.

An exemplary antioxidant B used herein includes tocopherol (e.g., α-tocopherol, β-tocopherol, γ-tocopherol, δ-tocopherol, etc.); tocopherol acetate; and butyl hydroxyanisole, and a preferable antioxidant B is α-tocopherol, β-tocopherol, γ-tocopherol, or δ-tocopherol, further preferably α-tocopherol.

The content of an antioxidant B in the formulation of the present invention ranges from 5 to 250 times, preferably from 12.5 to 125 times, further preferably from 20 to 50 times, further more preferably from 25 to 50 times, the weight of Compound A.

A lyophilized formulation of the present invention may be prepared by filling an emulsion to a vial, followed by lyophilization with a lyophilizer under conventional preparation conditions. A preparation condition herein includes, but not limited thereto, a condition wherein an emulsion is frozen at around −40° C. in a lyophilizer, followed by depressurization of the inside of the lyophilizer under vacuum with the temperature inside being to −20° C., and dried for around 10 to 80 hours; after the temperature inside being further to 25° C., the emulsion is further dried for around 10 to 30 hours.

One embodiment of the formulation of the present invention includes a lyophilized formulation of an emulsion comprising:

i) (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide (hereinafter, referred to as "Compound A"), or a pharmaceutically acceptable salt thereof;

ii) squalane;

iii) an antioxidant A selected from the group consisting of an ascorbate ester (e.g., L-ascorbic stearate, ascorbyl palmitate, etc.), an inorganic salt of ascorbic acid (e.g., potassium ascorbate, sodium ascorbate, calcium ascorbate, etc.), and ascorbic acid;

iv) an excipient A selected from the group consisting of a non-reducing sugar alcohol, provided that mannitol is excluded;

v) a hydrophilic surfactant; and vi) a lipophilic surfactant.

Another embodiment of the formulation of the present invention includes a lyophilized formulation of an emulsion, comprising:

i) (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide (hereinafter, referred to as "Compound A"), or a pharmaceutically acceptable salt thereof;

ii) squalane;

iii) an antioxidant A selected from the group consisting of an ascorbate ester (e.g., L-ascorbic stearate, ascorbyl palmitate, etc.), an inorganic salt of ascorbic acid (e.g., potassium ascorbate, sodium ascorbate, calcium ascorbate, etc.), and ascorbic acid;

iv) an excipient A selected from the group consisting of a non-reducing sugar and a sugar alcohol, provided that mannitol is excluded;

v) a hydrophilic surfactant such as polyoxyethylene sorbitan fatty acid esters (e.g., Polysorbate 20, Polysorbate 40, Polysorbate 60, Polysorbate 65, Polysorbate 80, etc.); polyoxyethylene hydrogenated castor oils (e.g., polyoxyethylene hydrogenated castor oil 10, polyoxyethylene hydrogenated castor oil 20, polyoxyethylene hydrogenated castor oil 40, polyoxyethylene hydrogenated castor oil 50, polyoxyethylene hydrogenated castor oil 60, etc.); and polyoxyethylene polyoxypropylene glycols (e.g., polyoxyethylene (42) polyoxypropylene (67) glycol, polyoxyethylene (54) polyoxypropylene (39) glycol, polyoxyethylene (105) polyoxypropylene (5) glycol, polyoxyethylene (124) polyoxypropylene (39) glycol, polyoxyethylene (160) polyoxypropylene (30) glycol, polyoxyethylene (196) polyoxypropylene (67) glycol, polyoxyethylene (200) polyoxypropylene (70) glycol, etc.);

vi) a lipophilic surfactant such as sorbitan fatty acid esters (e.g., sorbitan fatty acid ester, sorbitan monolaurate, sorbitan monopalmitate, sorbitan monostearate, sorbitan tristearate, sorbitan monooleate, sorbitan sesquioleate, sorbitan trioleate, medium-chain triglyceride, etc.); glycerin fatty acid esters (e.g., glycerin fatty acid ester, glyceryl monostearate, glyceryl monomyristate, glyceryl monooleate, glyceryl triisooctanoate, etc.); sucrose fatty acid esters (e.g., sucrose fatty acid ester, sucrose stearate, sucrose palmitate, etc.); and propylene glycol fatty acid esters (e.g., propylene glycol fatty acid ester, propylene glycol monostearate, etc.); and iii') an antioxidant B selected from the group consisting of tocopherol (e.g., α-tocopherol, β-tocopherol, γ-tocopherol, δ-tocopherol, etc.), tocopherol acetate, and butyl hydroxyanisole.

Still another embodiment of the formulation of the present invention includes a lyophilized formulation that does not comprise the antioxidant A of iii) but comprises iii') tocopherol (e.g., α-tocopherol, β-tocopherol, γ-tocopherol, δ-tocopherol, etc.) as an antioxidant. The tocopherol is preferably α-tocopherol.

The content of tocopherol in the formulation ranges from 5 to 250 times, preferably from 12.5 to 125 times, further preferably from 20 to 50 times, further more preferably from 25 to 50 times, the weight of Compound A.

The formulation may further comprise an additional antioxidant such as sodium thiosulfate and butyl hydroxyanisole.

The weight of Compound A in the formulation of the present invention ranges from 0.0001 to 0.65 times, preferably from 0.0002 to 0.35 times, further preferably from 0.0005 to 0.065 times, the weight obtained from excluding Compound A from the lyophilized formulation.

Regarding the $D_{90}$ value of particle size of oil droplets in the formulation of the present invention, the $D_{90}$ value of particle size of an emulsion during preparation is 1000 nm or less, preferably 300 nm or less. The Do value of particle size of oil droplets of an emulsion reconstituted after storage as the lyophilized formulation is preferably 1000 mm or less for the $D_{90}$ value of particle size of oil droplets of an emulsion reconstituted after 6-month storage at 5° C. or 25° C.

The $D_{90}$ value of particle size of oil droplets in the formulation of the present invention is one of representative values showing the particle size distribution of oil droplet particles comprised in an emulsion, and means a 90% particle size based on the scattering intensity. The $D_{90}$ value of particle size is generally calculated by measurement with an analyzer such as a dynamic light-scattering particle size analyzer, a laser diffraction particle size analyzer, and a particle size analyzer by image processing technique. The $D_{90}$ value of particle size herein means the value measured with a dynamic light-scattering particle size analyzer: Zetasizer Nano ZS (Malvern).

In the formulation of the present invention, an impurity UK-1.02 is one of typical impurities detected in the assessment of related substances with a high-performance liquid chromatograph. It means an impurity that is detected at 1.02-fold the elution time of Compound A in spectroscopic measurement by reversed-phase high performance liquid chromatography under a 220-nm wavelength with a Phenyl-Hexyl column (Waters, Xselect CSH Phenyl-Hexyl XP Column, 4.6 mm×75 mm, 2.5 μm, Model No.: 186006134) injected with an amount corresponding to 0.4 to 2 μg of Compound A and eluted with pure water, acetonitrile, methanol, and trifluoroacetic acid. Details of the measurement condition are as follows.

Mobile phase A: 0.1% trifluoroacetic acid aqueous solution

Mobile phase B: acetonitrile/methanol mixed solution (8:2) comprising 0.06% trifluoroacetic acid Delivery Condition:

| Time (min.) | Mobile phase A:Mobile phase B |
|---|---|
| 0.0 to 0.5 | 6:4 |
| 0.5 to 50.5 | 6:4 to 1:9 |
| 50.5 to 65.0 | 1:9 |
| 65.0 to 65.1 | 1:9 to 6:4 |
| 75.0 | 6:4 |

Flow rate: 0.5 mL/min.

Column temperature: a certain temperature around 40° C.

In terms of the preservation stability of the formulation of the present invention, the area percentage value of the impurity UK-1.02 increases 5.0% or less, preferably 1.0% or less, of the value at the start of the storage after 6-month storage of a lyophilized formulation of the present invention at 5° C. The area percentage values are compared in an actual measured value.

A formulation of the present invention is stored in its lyophilized form after an oil-in-water emulsion prepared is emulsified, followed by aseptic filtration with a sterile filter and lyophilization. In the aseptic filtration, it is preferable that the $D_{90}$ value of particle size of the emulsion is 1000 nm or less in terms of avoidance of clogging and efficient filtration.

A formulation of the present invention may comprise an additional additive as long as the particle size of the emulsion does not change between before and after reconstitution. The formulation may be administered by mixing with a formulation comprising a vaccine antigen when administered as long as the particle size of the emulsion does not change between and after reconstitution. The way of mixing and the mixing ratio of the formulation of the present invention and a vaccine antigen are not limited; for example, a reconstituted emulsion formulation may be mixed with an equal volume of a formulation comprising a vaccine antigen by inversion of a vial.

The vaccine antigen administered in a mixture with the formulation of the present invention includes, but not limited thereto, for example, an antigen protein, an antigen peptide (partial peptide) derived from the antigen protein, and a complex thereof with a carrier. Examples of the vaccine antigen include 1) tumor antigen proteins or tumor antigen peptides for cancer immunotherapy, and 2) active ingredients of vaccines for prevention of infection. The carrier refers to a substance that chemically and/or physically combines an antigen protein or antigen peptide, and for example, includes proteins and lipids.

A formulation of the present invention may be provided as a kit comprising a lyophilized formulation comprising Compound A and a vaccine antigen.

A formulation of the present invention may be reconstituted with 2 to 20-fold of sterile water for injection by weight of a lyophilized formulation upon administration, and may be administered in a mixture with a formulation comprising a vaccine antigen. A dosage amount of the formulation of the present invention per each administration ranges from 1 ng to 250 mg, preferably from 1 ng to 50 mg, calculated as the weight of Compound A. The frequency of administration varies depending on the kind of a vaccine antigen to be co-administered or the age of a subject to be administered, but may be a single administration or may include one or more of additional administrations.

According to the present invention, the preservation stability was shown by the Test examples as below.

EXAMPLES

The present invention is illustrated by Examples, Reference examples, Comparative examples, and Test examples as below, but is not limited thereto.

"Squalane (Wako Pure Chemical Corporation)", "Squalane (Kishimoto Special Liver Oil Co., Ltd.)", or "Squalane (Maruha Nichiro Corporation)" was used for squalane; "Squalene (Wako Pure Chemical Corporation)", "Squalene (Kishimoto Special Liver Oil Co., Ltd.)", or "Squalene (Maruha Nichiro Corporation)" was used for squalene; "Sodium ascorbate (Wako Pure Chemical Corporation)" or "Sodium L-ascorbate (Kyowa Pharma Chemical Co., Ltd.)" was used for sodium ascorbate; "α-Tocopherol (Mitsubishi Chemical Foods)" or "all-rac-α-Tocopherol EMPROVE (registered trademark) ESSENTIAL Ph Eur, BP, USP, E 307 (Merck)" was used for α-tocopherol; "Span 85 (Sigma-Aldrich, Inc.)", "RHEODOL SP-O30V (Kao Corporation)", or "Span 85 (CRODA)" was used for sorbitan trioleate; "PS80 (GS) (NOF Corporation)", "Polysorbate 80 (HX2) (NOF Corporation)", "Tween 80 (Merck)", or "Tween 80 HP-LQ-(HM) (CRODA)" was used for Polysorbate 80; "Sucrose (Nacalai Tesque)" or "Sucrose low in endotoxins suitable for use as excipient EMPROVE (registered trademark) exp Ph Eur, BP, JP, NF (Merck)" was used for sucrose; "Otsuka distilled water (Otsuka Pharmaceutical Factory, Inc.)" was used for sterile water for injection; and ascorbyl palmitate, butyl hydroxyanisole, and sodium thiosulfate from Wako Pure Chemical Corporation were used.

[Preparation of Lyophilized Compositions]

Examples 1 to 16, Comparative Examples 1 to 3

Compound A was dissolved in oil ingredients (Examples 1 to 9, and 15: squalane, sorbitan trioleate, and α-tocopherol; Examples 10 to 13: squalane and sorbitan trioleate; Example 14: squalane, sorbitan trioleate, α-tocopherol, and ascorbyl palmitate; Example 16: squalane, sorbitan trioleate, α-tocopherol, and butyl hydroxyanisole; Comparative examples 1 to 3: squalene, sorbitan trioleate, and α-tocopherol), resulting in the compositions in Tables 1 to 4. Aqueous ingredients (Examples 1 to 3, 14, and 16: sucrose and Polysorbate 80; Examples 4 to 13: sucrose, Polysorbate 80, and sodium ascorbate; Example 15: sucrose, Polysorbate 80, and sodium thiosulfate) was dissolved in sterile water for injection, resulting in the compositions in Tables 1 to 4, and then thereto was added each of the above-mentioned oil compositions. The mixture was premixed, and emulsified to be dispersed with a high-pressure emulsification dispersion device. The mixture was filtered through a 0.2-μm-sterilizing filter, and then filled in glass vials in 1 mL each, followed by lyophilization. Each vial was backfilled with nitrogen gas to ordinary pressure, and then the vials were sealed with rubber stoppers to give lyophilized compositions, Examples 1 to 16 and Comparative examples 1 to 3.

TABLE 1

| Ingredients | Example 1 | Example 2 | Example 3 | Example 4 | Example 5 | Example 6 | Example 7 |
|---|---|---|---|---|---|---|---|
| Compound A | 1 | 1 | 1 | 1 | 1 | 1 | 1 |
| squalane | 225 | 200 | 237.5 | 225 | 225 | 225 | 225 |
| α-tocopherol | 25 | 50 | 12.5 | 25 | 25 | 25 | 25 |
| sodium ascorbate | 0 | 0 | 0 | 2.5 | 5 | 10 | 20 |
| ascorbyl palmitate | 0 | 0 | 0 | 0 | 0 | 0 | 0 |
| sorbitan trioleate | 25 | 25 | 25 | 25 | 25 | 25 | 25 |
| Polysorbate 80 | 25 | 25 | 25 | 25 | 25 | 25 | 25 |
| sucrose | 500 | 500 | 500 | 500 | 500 | 500 | 500 |

Note)
Each value refers to a weight ratio of each ingredient to 1 weight part of Compound A.

TABLE 2

| Ingredients | Example 8 | Example 9 | Example 10 | Example 11 | Example 12 | Example 13 | Example 14 |
|---|---|---|---|---|---|---|---|
| Compound A | 1 | 1 | 1 | 1 | 1 | 1 | 1 |
| squalane | 225 | 225 | 250 | 250 | 250 | 250 | 225 |
| α-tocopherol | 25 | 25 | 0 | 0 | 0 | 0 | 25 |
| sodium ascorbate | 40 | 60 | 10 | 20 | 40 | 60 | 0 |
| ascorbyl palmitate | 0 | 0 | 0 | 0 | 0 | 0 | 0.5 |
| sorbitan trioleate | 25 | 25 | 25 | 25 | 25 | 25 | 25 |
| Polysorbate 80 | 25 | 25 | 25 | 25 | 25 | 25 | 25 |
| sucrose | 500 | 500 | 500 | 500 | 500 | 500 | 500 |

Note)
Each value refers to a weight ratio of each ingredient to 1 weight part of Compound A.

TABLE 3

| Ingredients | Example 15 | Example 16 |
|---|---|---|
| Compound A | 1 | 1 |
| squalane | 225 | 225 |
| α-tocopherol | 25 | 25 |
| sodium ascorbate | 0 | 0 |
| sodium thiosulfate | 5 | 0 |
| butyl hydroxyanisole | 0 | 0.25 |
| sorbitan trioleate | 25 | 25 |
| Polysorbate 80 | 25 | 25 |
| sucrose | 500 | 500 |

Note)
Each value refers to a weight ratio of each ingredient to 1 weight part of Compound A.

TABLE 4

| Ingredients | Comparative example 1 | Comparative example 2 | Comparative example 3 |
|---|---|---|---|
| Compound A | 1 | 1 | 1 |
| squalene | 237.5 | 225 | 200 |
| squalane | 0 | 0 | 0 |
| α-tocopherol | 12.5 | 25 | 50 |
| sodium ascorbate | 0 | 0 | 0 |
| sorbitan trioleate | 25 | 25 | 25 |
| Polysorbate 80 | 25 | 25 | 25 |
| sucrose | 500 | 500 | 500 |

Note)
Each value refers to a weight ratio of each ingredient to 1 weight part of Compound A.

[Test Example 1] Measurement of Particle Sizes During the Preparation Process In the preparation process of a lyophilized composition, the particle size distribution of oil droplet particles comprised in an emulsion after emulsification and before lyphilization was measured in the following manner.

An emulsion was diluted 10 times with sterile water for injection, and the 90% particle size ($D_{90}$) based on the intensity was measured with a dynamic light-scattering scattering particle size analyzer (Zetasizer Nano ZS). $D_{90}$ (nm) of Examples 1 to 16 and Comparative examples 1 to 3 are shown in Table 5.

TABLE 5

| | Example 1 | Example 2 | Example 3 | Example 4 | Example 5 | Example 6 | Example 7 | Example 8 |
|---|---|---|---|---|---|---|---|---|
| $D_{90}$ (nm) | 294 | 276 | 274 | 273 | 287 | 293 | 270 | 250 |
| | Example 9 | Example 10 | Example 11 | Example 12 | Example 13 | Example 14 | Example 15 | Example 16 |
| $D_{90}$ (nm) | 259 | 280 | 288 | 279 | 266 | 289 | 290 | 295 |

TABLE 5-continued

| | Comparative example 1 | Comparative example 2 | Comparative example 3 |
|---|---|---|---|
| $D_{90}$ (nm) | 280 | 309 | 273 |

[Test Example 2] Stability Assessment (1)

The particle size distributions of the lyophilized compositions as prepared were measured in the following manner before and after 6-month storage in a constant temperature incubator at 5° C. and 25° C.

Each vial of lyophilized compositions prepared in Examples 1 to 16 and Comparative examples 1 to 3 was reconstituted by addition of 1 mL each of sterile water for injection, and then 100 μL of a drug solution after the reconstitution was taken with a micropipette. The taken drug solution was mixed with 900 μL of sterile water for injection, and then the 90% particle size ($D_{90}$) based on the scattering intensity was measured with a dynamic light-scattering particle size analyzer (Zetasizer Nano ZS). $D_{90}$ (nm) of Examples 1 to 16 and Comparative examples 1 to 3 before and after the storage are shown in Table 6.

TABLE 6

| | Example 1 | Example 2 | Example 3 | Example 4 | Example 5 | Example 6 | Example 7 | Example 8 |
|---|---|---|---|---|---|---|---|---|
| Initial | 655 | 915 | 738 | 594 | 586 | 624 | 594 | 565 |
| 5° C. 6M | 598 | 618 | 553 | 575 | 590 | 792 | 558 | 529 |
| 25° C. 6M | 3300 | 1810 | 4650 | 772 | 599 | 946 | 606 | 502 |

| | Example 9 | Example 10 | Example 11 | Example 12 | Example 13 | Example 14 | Example 15 | Example 16 |
|---|---|---|---|---|---|---|---|---|
| Initial | 564 | 662 | 621 | 562 | 554 | 665 | 698 | 694 |
| 5° C. 6M | 600 | 610 | 601 | 508 | 544 | 508 | 585 | 576 |
| 25° C. 6M | 937 | 594 | 551 | 488 | 477 | 505 | 837 | 1150 |

| | Comparative example 1 | Comparative example 2 | Comparative example 3 |
|---|---|---|---|
| Initial | 675 | 552 | 1020 |
| 5° C. 6M | 579 | 631 | 625 |
| 25° C. 6M | 5880 | 969 | 1040 |

According to the test results, the formulations of Examples 4 to 14 comprising an antioxidant of ascorbates showed few changes in the particle size distribution after 6-month storage in a constant temperature incubator at 5° C. and 25° C. compared to the initial value, and these formulations are considered to have high stability in the particle size distribution.

[Test Example 3] Stability Assessment (2)

For a lyophilized composition as prepared, the amount of an impurity (i.e., the area percentage value of Uk-1.02) was measured in the following manner before and after 6-month storage in a constant temperature incubator at 5° C.

The impurity was spectroscopically detected by reversed-phase high performance liquid chromatography under a 220-nm wavelength with a Phenyl-Hexyl column (Waters, Xselect CSH Phenyl-Hexyl XP Column, 4.6 mm×75 mm, 2.5 μm, Model No.: 186006134) injected with an amount corresponding to 0.4 to 2 μg of Compound A and eluted with pure water, acetonitrile, methanol, and trifluoroacetic acid. Details of the measurement condition are as follows.

Mobile phase A: 0.1% trifluoroacetic acid aqueous solution

Mobile phase B: acetonitrile/methanol mixed solution (8:2) comprising 0.06% trifluoroacetic acid Elution Condition:

| Time (min) | Mobile phase A: Mobile phase B |
|---|---|
| 0.0 to 0.5 | 6:4 |
| 0.5 to 50.5 | 6:4 to 1:9 |
| 50.5 to 65.0 | 1:9 |
| 65.0 to 65.1 | 1:9 to 6:4 |
| 75.0 | 6:4 |

Flow rate: 0.5 mL/min

Column temperature: a constant temperature around 40° C.

The area percentage value of a peak of an impurity (Uk-1.02) detected at a 1.02-fold elution time of Compound A was calculated in the following equation with the peak area and elution time measured herein.

Area percentage value (%) of $Uk$-1.02Peak area of $Uk$-1.02/Total peak area of related substances and Compound $A \times 100$ The area percentage values (%) of peaks of impurities (Uk-1.02) in Examples 1 to 16 and Comparative examples 1 to 3 before and after storage are shown in Table 7.

TABLE 7

| | Example 1 | Example 2 | Example 3 | Example 4 | Example 5 | Example 6 | Example 7 | Example 8 |
|---|---|---|---|---|---|---|---|---|
| Initial | 1.3 | 0.9 | <0.1 | 0.9 | 0.8 | 0.9 | 0.8 | <0.1 |
| 5° C. 6M | 2.4 | 2.4 | 4.6 | 1.0 | 0.9 | 0.9 | 0.8 | 0.6 |

| | Example 9 | Example 10 | Example 11 | Example 12 | Example 13 | Example 14 | Example 15 | Example 16 |
|---|---|---|---|---|---|---|---|---|
| Initial | 0.6 | <0.1 | <0.1 | <0.1 | <0.1 | 0.7 | 1.7 | 1.4 |
| 5° C. 6M | 0.5 | 0.3 | 0.3 | 0.4 | 0.4 | 0.8 | 3.7 | 2.8 |

| | Comparative example 1 | Comparative example 2 | Comparative example 3 |
|---|---|---|---|
| Initial | 1.0 | 0.8 | 1.1 |
| 5° C. 6M | 27.1 | 9.4 | 7.7 |

According to the test results, the formulations of Examples 4 to 14 comprising an antioxidant of ascorbates showed low values of an impurity (area percentage value of Uk-1.02) after 6-month storage in a constant temperature incubator at 5° C., and these formulations are considered to have high preservation stability. In a comparison of the formulations of Examples 1 to 3 comprising squalane for an oil ingredient with the formulations of Comparative examples 1 to 3 comprising squalene for an oil ingredient, the formulations comprising squalane as an oil ingredient showed a lower value of an impurity (area percentage value of Uk-1.02) than the other formulations, and squalane is considered to contribute to the stability in the antioxidative action of Compound A and the formulations comprising squalane are considered to have high preservation stability.

INDUSTRIAL APPLICABILITY

According to these Examples, Reference examples, Comparative examples, and Test examples, the formulation of the present invention has high preservation stability, and is used for a vaccine adjuvant formulation.

The invention claimed is:

1. A lyophilized formulation of an emulsion comprising:

i) (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide (Compound A), or a pharmaceutically acceptable salt thereof;

ii) squalane;

iii) an antioxidant A selected from the group consisting of an ascorbate ester, an inorganic salt of ascorbic acid, and ascorbic acid; and iv) an excipient A selected from the group consisting of a non-reducing sugar and a sugar alcohol, provided that mannitol is excluded;

wherein the $D_{90}$ value of particle sizes of an emulsion reconstituted after 6-month storage at 5° C. as the lyophilized formulation is 1000 nm or less;

wherein the amount of squalane in the formulation is 200 to 300 times the weight of Compound A in the formulation;

wherein the amount of the antioxidant A in the formulation is 5 to 100 times the weight of Compound A in the formulation, in terms of the weight of sodium ascorbate; and wherein the amount of the excipient A in the formulation is 200 to 625 times the weight of Compound A in the formulation.

2. The formulation according to claim 1, further comprising v) a hydrophilic surfactant and vi) a lipophilic surfactant.

3. The formulation according to claim 1, wherein the emulsion is an oil-in-water emulsion.

4. The formulation according to claim 2, wherein the hydrophilic surfactant is polyoxyethylene sorbitan fatty acid esters, polyoxyethylene hydrogenated castor oils, or polyoxyethylene polyoxypropylene glycols.

5. The formulation according to claim 2, wherein the hydrophilic surfactant is Polysorbate 20, Polysorbate 40, Polysorbate 80, polyoxyethylene hydrogenated castor oil 60, or polyoxyethylene (160) polyoxypropylene (30) glycol.

6. The formulation according to claim 2, wherein the hydrophilic surfactant is Polysorbate 20, Polysorbate 40, or Polysorbate 80.

7. The formulation according to claim 2, wherein the lipophilic surfactant is sorbitan fatty acid esters, glycerin fatty acid esters sucrose fatty acid esters, or propylene glycol fatty acid esters.

8. The formulation according to claim 2, wherein the lipophilic surfactant is sorbitan fatty acid ester, sorbitan monooleate, sorbitan sesquioleate, or sorbitan trioleate.

9. The formulation according to claim 2, wherein the lipophilic surfactant is sorbitan trioleate.

10. The formulation according to claim 1, further comprising an antioxidant B selected from the group consisting of tocopherol, tocopherol acetate, and butyl hydroxyanisole.

11. The formulation according to claim 10, wherein the antioxidant B is α-tocopherol.

12. The formulation according to claim 1, wherein the antioxidant A is ascorbyl palmitate, potassium ascorbate, sodium ascorbate, or ascorbic acid.

13. The formulation according to claim 1, wherein the antioxidant A is sodium ascorbate or potassium ascorbate.

14. The formulation according to claim 1, wherein the excipient A is a non-reducing sugar selected from sucrose and trehalose or a sugar alcohol selected from sorbitol, erythritol, xylitol, maltitol, and lactitol.

15. The formulation according to claim 2, wherein the amount of the hydrophilic surfactant in the formulation is 0.5 to 250 times the weight of the (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide, or a pharmaceutically acceptable salt thereof, in the formulation.

16. The formulation according to claim 2, wherein the amount of the lipophilic surfactant in the formulation is 0.5 to 250 times the weight of the (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide, or a pharmaceutically acceptable salt thereof, in the formulation.

17. The formulation according to claim 10, wherein the amount of the blending antioxidant B in the formulation is 5 to 250 times the weight of the (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide, or a pharmaceutically acceptable salt thereof, in the formulation.

18. The formulation according to claim 1, wherein the weight of the (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide, or a pharmaceutically acceptable salt thereof, is 0.0001 to 0.65 times the weight obtained by excluding the (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide, or a pharmaceutically acceptable salt thereof, from the lyophilized formulation.

19. The formulation according to claim 1, wherein both $D_{90}$ values of particle sizes of an emulsion immediately after preparation and an emulsion reconstituted after 6-month storage at 25° C. as the lyophilized formulation are 1000 nm or less.

20. The formulation according to claim 1, wherein an increased amount in the area percentage values of an impurity UK-1.02 after 6-month storage at 5° C. as the lyophilized formulation is 5.0% or less.

21. A vaccine adjuvant comprising the formulation according to claim 1.

22. A vaccine comprising the formulation according to claim 1 and an antigen.

23. The vaccine according to claim 22, wherein the antigen is derived from a pathogen.

24. A kit comprising the formulation according to claim 1 and an antigen.

25. The formulation according to claim 1, wherein a $D_{90}$ value of particle sizes of an emulsion reconstituted after 6-month storage at 25° C. as the lyophilized formulation is 2-fold or less than a $D_{90}$ value of particle sizes of an emulsion immediately after preparation.

26. The formulation according to claim 1, wherein a $D_{90}$ value of particle sizes of an emulsion during preparation is 1000 nm or less.

27. The formulation according to claim 1, wherein a $D_{90}$ value of particle sizes of an emulsion at the start time of lyophilization storage is 1000 nm or less.

28. The formulation according to claim 1, wherein a $D_{90}$ value of particle sizes of an emulsion reconstituted after 6-month storage at 25° C. as the lyophilized formulation is 1000 nm or less.

* * * * *